(12) United States Patent
Basu et al.

(10) Patent No.: US 11,944,335 B2
(45) Date of Patent: Apr. 2, 2024

(54) ENDOSCOPIC MEDICAL DEVICE AND METHOD OF USE

(71) Applicant: Boston Scientific Limited, Hamilton (BM)

(72) Inventors: Abhishek Basu, Haryana (IN); Agrim Mishra, Delhi (IN); Deepak Kumar Sharma, Muzaffarnafar (IN); Hitendra Purohit, Guj (IN); Rohit Rohilla, Haryana (IN)

(73) Assignee: Boston Scientific Medical Device Limited, Galway (IE)

( * ) Notice: Subject to any disclaimer, the term of this patent is extended or adjusted under 35 U.S.C. 154(b) by 0 days.

(21) Appl. No.: 16/876,390

(22) Filed: May 18, 2020

(65) Prior Publication Data

US 2020/0367921 A1 Nov. 26, 2020

Related U.S. Application Data

(60) Provisional application No. 62/850,186, filed on May 20, 2019.

(51) Int. Cl.
*A61B 17/29* (2006.01)
*A61B 17/00* (2006.01)
*A61B 17/3201* (2006.01)

(52) U.S. Cl.
CPC .... *A61B 17/29* (2013.01); *A61B 2017/00292* (2013.01); *A61B 2017/2902* (2013.01); *A61B 17/2909* (2013.01); *A61B 2017/2936* (2013.01); *A61B 17/3201* (2013.01)

(58) Field of Classification Search
CPC . A61B 17/29; A61B 17/2909; A61B 17/3201; A61B 2017/00292; A61B 2017/2902; A61B 2017/2936; A61B 2017/2927; A61B 2017/2934; A61B 2017/2939; A61B 10/06
See application file for complete search history.

(56) References Cited

U.S. PATENT DOCUMENTS

| | | | |
|---|---|---|---|
| 5,238,002 A | 8/1993 | Devlin et al. | |
| 5,906,630 A | 5/1999 | Anderhub et al. | |
| 5,971,940 A | 10/1999 | Baker et al. | |
| 6,743,185 B2 | 6/2004 | Weber et al. | |
| 7,621,910 B2 * | 11/2009 | Sugi | A61B 18/1445 606/51 |
| 7,762,960 B2 | 7/2010 | Timberlake et al. | |
| 7,951,165 B2 | 5/2011 | Golden et al. | |
| 9,198,683 B2 | 12/2015 | Friedman et al. | |
| 10,154,801 B2 | 12/2018 | Friedman et al. | |

(Continued)

OTHER PUBLICATIONS

International Search Report and Written Opinion issued in PCT/IB2020/054702 dated Nov. 16, 2021 (8 pages).

*Primary Examiner* — Brooke Labranche
(74) *Attorney, Agent, or Firm* — Bookoff McAndrews PLLC

(57) ABSTRACT

A medical device includes opposing first and second end effectors coupled together to move from an open configuration to a closed configuration, a first link with a distal end pivotally connected to a proximal end of the first end effector, the first link including a first slot at a proximal end of the first link, a second link with a distal end pivotally connected to a proximal end of the second end effector, and a first actuator pin slidable within the first slot.

19 Claims, 6 Drawing Sheets

(56) References Cited

U.S. PATENT DOCUMENTS

| | | | |
|---|---|---|---|
| 2005/0101991 A1 | 5/2005 | Ahlberg et al. | |
| 2006/0258954 A1* | 11/2006 | Timberlake | A61B 10/06 |
| | | | 606/205 |
| 2007/0073185 A1 | 3/2007 | Nakao | |
| 2010/0057085 A1 | 3/2010 | Holcomb et al. | |
| 2015/0342585 A1 | 12/2015 | Steege | |
| 2019/0143535 A1 | 5/2019 | Rockrohr | |
| 2019/0192215 A1* | 6/2019 | Kerr | A61B 17/29 |
| 2019/0365458 A1* | 12/2019 | Whitlock | A61B 34/30 |

* cited by examiner

ENDOSCOPIC MEDICAL DEVICE AND METHOD OF USE

CROSS-REFERENCE TO RELATED APPLICATIONS

This application claims the benefit of priority from U.S. Provisional Application No. 62/850,186, filed May 20, 2019, which is incorporated by reference herein in its entirety.

TECHNICAL FIELD

The present disclosure relates generally to endoscopic medical devices and methods of use. More particularly, in some embodiments, the disclosure relates to devices for grasping and manipulating tissue, and methods for targeting, accessing, and acquiring tissue samples for, e.g., histology analysis or other analysis techniques.

BACKGROUND

Conventional biopsy devices are generally advanced through a catheter, endoscope, or other like device, to a desired location in a patient. The size of the distal assembly of the device, including the cutting and grabbing mechanism, may provide unsatisfactory tissue acquisition, or make passability through a tortuous path difficult.

Accordingly, methods of acquiring tissue using conventional biopsy devices may require more tissue samples to be acquired to ensure the quality of the sample is sufficient for analysis. Additional samples, however, can cause additional trauma by removing more tissue than is necessary from the body, and may increase the procedure time, thereby increasing costs and/or exposing the patient to additional risks. Further, conventional biopsy devices may be unable to access certain areas of the body due to a tortuous path leading to the treatment site, requiring additional trauma to access these regions. The present disclosure may solve one or more of these problems or other problems in the art. The scope of the disclosure, however, is defined by the attached claims and not the ability to solve a specific problem.

SUMMARY OF THE DISCLOSURE

According to an embodiment, a medical device includes opposing first and second end effectors coupled together to move from an open configuration to a closed configuration, a first link with a distal end pivotally connected to a proximal end of the first end effector, the first link including a first slot at a proximal end of the first link, a second link with a distal end pivotally connected to a proximal end of the second end effector, and a first actuator pin slidable within the first slot.

The second link may include a second slot at a proximal end thereof, and the medical device may further include a second actuator pin, connected to the first actuator pin, and slidable within the second slot.

The first slot may move over the first actuator pin when the first actuator pin is stationary and when the first and the second end effectors are in the open configuration, and the first end effector may pivot about the axis of the pivot pin while the second end effector remains stationary, and the second slot may move over the second actuator pin when the second actuator pin is stationary and when the first and the second end effectors are in the open configuration, and the second end effector may pivot about the axis of the pivot pin while the first end effector remains stationary.

The first and second end effectors may pivot about an axis of a pivot pin when the first actuator pin is stationary and the first and the second end effectors are in the closed configuration.

The first slot may move over the first actuator pin when the first actuator pin is stationary, and the first and the second end effectors may pivot about the axis of the pivot pin when in the closed configuration.

The second slot may move over the second actuator pin when the second actuator pin is stationary, and the first and the second end effectors may pivot about the axis of the pivot pin when in the closed configuration.

Each of the first slot and the second slot may be curved.

The first slot may include two concave ends, the concave ends facing each other and connected by a first concave sidewall and a second convex sidewall opposite the first concave sidewall, and the first slot may be angled with respect to the distal end of the first link.

The medical device may further include a catheter including a lumen extending along a longitudinal axis of the catheter, the catheter may be connected to the first and second end effectors at a distal end of the catheter, and a wire may extend through the lumen and may be coupled to the first actuator pin, wherein movement of the wire along the longitudinal axis may cause the first and the second end effectors to move between the open configuration and the closed configuration.

A longitudinal axis of the first and the second end effectors may be angled relative to the longitudinal axis of the catheter, when the first and the second end effectors may be in the closed configuration.

The first and the second end effectors may be fixed to the catheter.

Distal ends of the first and second end effectors may rotate to a first position above the longitudinal axis of the catheter and to a second position below the longitudinal axis of the catheter, when the first and second end effectors are in the closed configuration.

The first slot may include two concave ends, the concave ends facing each other and connected by a first concave sidewall and a second convex sidewall opposite the first concave sidewall, and the first slot may be substantially parallel to a throughhole in the distal end of the first link.

The first link may include a first hole at the distal end of the first link, the first hole may be sized to receive a first pin on the first end effector.

The medical device may further include a clevis, wherein the first and second end effectors may be pivotally connected to a distal end of the clevis, wherein the clevis may include a pair of distally extending and spaced apart arms, each of the pair of arms may include a hole, and wherein the medical device further includes a pin fixedly attached to the hole in each of the pair of arms, the first and second end effectors may be pivotally connected about an axis of the pin.

According to another embodiment, a medical device includes opposing first and second end effectors coupled together and configured to move from a fully open configuration to a closed configuration, and a clevis operably connected to the first and the second end effectors, the clevis includes a body and a pair of arms extending distally from the body and defining a slot between the pair of arms, the clevis further including a pair of sidewalls at a proximal end of the slot where the slot meets the body, where the sidewalls are transverse to a longitudinal axis of the clevis and restrict the first and the second end effectors from opening past the fully open configuration.

The clevis may include a throughhole in a distal end of each of the pair of arms, a pin coupled to the throughhole of each of the pair of arms, and a slot in a proximal end of each of the pair of arms and extending along the longitudinal axis of the clevis, and an actuator operably coupled to the first and the second end effectors, wherein the actuator may extend into the slot in each of the pair of arms and may actuate the first and the second end effectors between the fully open configuration and the closed configuration.

According to yet another embodiment, a method for performing an operation in a body includes inserting first and second end effectors into the body when the first and the second end effectors are in a closed configuration, pivoting both of the first end effector and the second end effector about a pivot axis to transform the first and the second end effectors from the closed configuration to an open configuration, either one or both of: (1) further pivoting the first end effector about the pivot axis as the second end effector does not pivot about the pivot axis, and (2) pivoting the first end effector toward a longitudinal axis of the end effectors and, at the same time, pivoting the second end effector away from the longitudinal axis, with the first and the second end effectors in the open configuration, and closing the first end effector relative to the second end effector, with tissue between the first end effector and the second end effector.

The method may further include rotating the first end effector or the second end effector about the pivot axis after the other of the first end effector or the second end effector contacts tissue.

The method may further include advancing the first and second end effectors along an inner lumen of a catheter, and while the first and second end effectors are disposed within the inner lumen, pivoting the first end effector toward a longitudinal axis of the end effectors and, at the same time, pivoting the second end effector away from the longitudinal axis, with the first and the second end effectors in the closed configuration.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Figure 1:
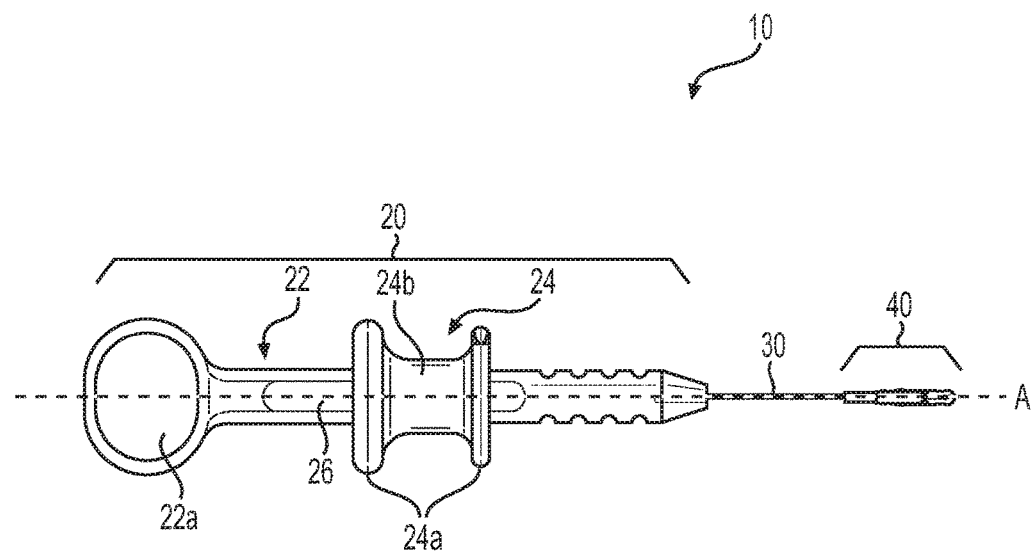
FIG. 1 is a schematic of a medical device according to an embodiment.

Referring to FIG. 1, a medical device 10 (e.g., a biopsy device) according to an embodiment is shown. Medical device 10 includes a handle 20, a catheter 30 connected to handle 20, and an end effector assembly 40 (e.g., a biopsy assembly) at a distal end of catheter 30, opposite handle 20.

With continued reference to FIG. 1, handle 20 is illustrated. Handle 20 includes a body 22 defining a hole 22a in body 22 at a proximal end thereof. Catheter 30 is attached at an opposite, distal end of body 22. A slot 26 extends through body 22 in a direction parallel to a longitudinal axis A of catheter 30. A spool 24 is disposed in slot 26 and moves within slot 26 and along body 22 in a direction parallel to longitudinal axis A. As further shown in FIG. 2, spool 24 includes two annular protrusions 24a at a distal end and a proximal end thereof and extending from spool 24 in a direction perpendicular to the direction of longitudinal axis A and the extension of catheter 30. Annular protrusions 24a define an annular grip 24b, which is grasped by a user as will be described in greater detail herein. It will be understood that handle 20 may be made of any material known in the art, including, but not limited to, a medical grade plastic or rubber, a ceramic, a metal, or a combination thereof. It will also be understood that handle 20 is not limited to the configuration shown in FIG. 1. For example, handle 20 may be any actuating handle known in the art, including, but not limited to, the devices disclosed in U.S. Pat. Nos. 6,743,185 and/or 7,762,960, the contents of each of which are incorporated herein by reference in their entirety.

Figure 2:
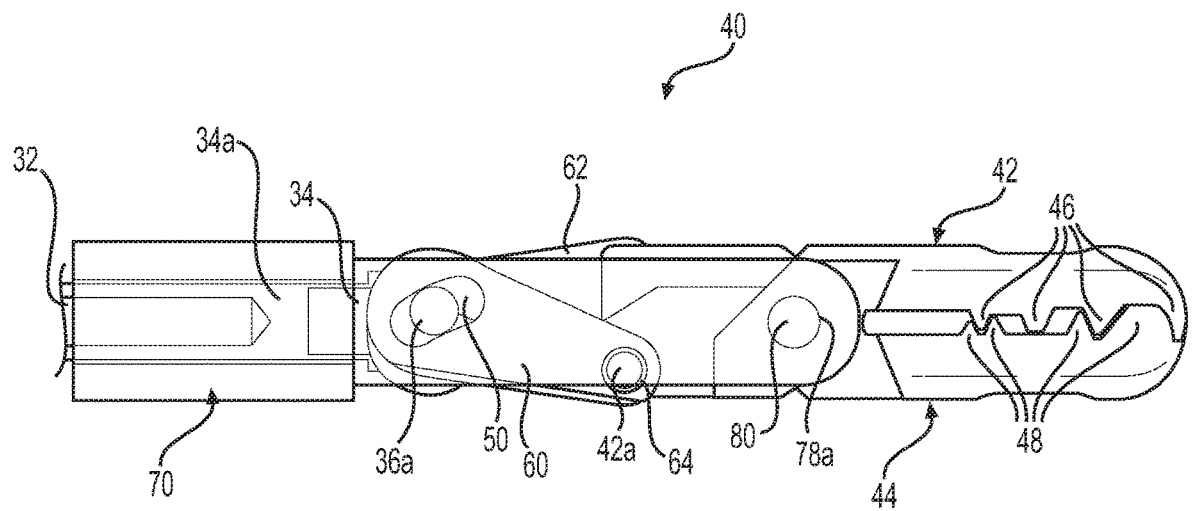
FIG. 2 is a plain view of an end effector assembly of the medical device according to an embodiment.

A wire 32 (the distal end of which is shown in FIG. 2) extends distally from the distal end of spool 24. Wire 32 extends through a hole (not shown) at the distal end of body 22 and into a lumen (not shown) of catheter 30. As will be described in greater detail herein, actuation of wire 32 actuates end effectors (e.g., cutting members) of end effector assembly 40. As will be understood, catheter 30 is a generally circular sheath extending from handle 20 along longitudinal axis A, and may be any length suitable for performing a medical procedure, with end effector assembly 40 extending from a distal end thereof. While catheter 30 is described as including a lumen (not shown), catheter 30 may include multiple lumens to accommodate other actuators, wires, and/or lighting or imaging elements. Additionally, or alternatively, catheter 30 may be placed in another, larger catheter endoscope, colonoscope, bronchoscope, ureteroscope, sheath, or other like-device (not shown), if use of tools, suction, light-emitting elements, imaging, or the like associated with the larger catheter are desired. It will be understood that wire 32 may include any material known in the art, including, but not limited to, medical grade plastic, metal, or other resin suitable for actuating and/or maneuvering end effector assembly 40, as described herein, during medical procedures. Further, it will be understood that catheter 30 may be formed of any medical grade plastic, rubber, resin, or the like that is suitable for use in medical applications.

Figure 3A:
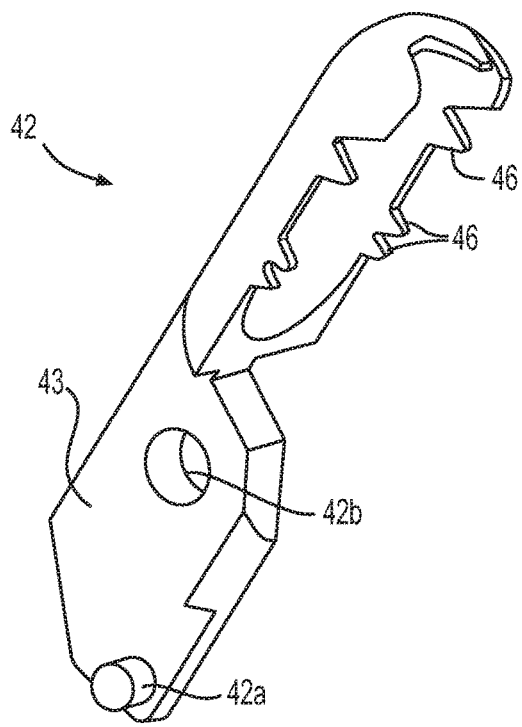
FIGS. 3A and 3B are perspective views of end effectors of the medical device of FIG. 2.
Figure 3B:
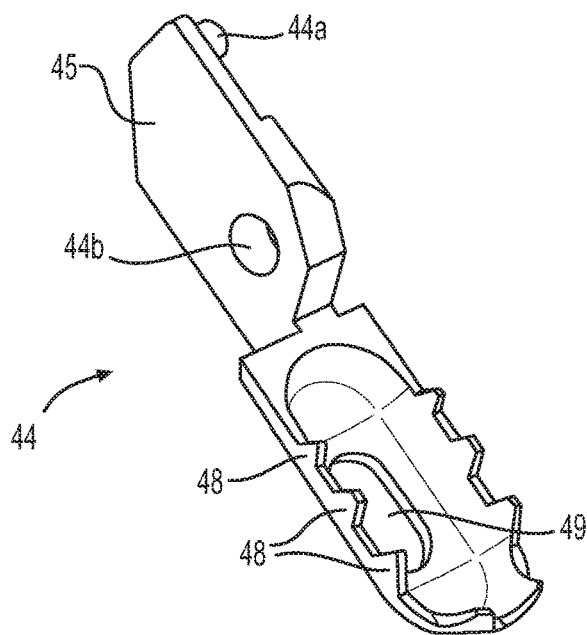

Referring to FIG. 2, end effector assembly 40 according to an embodiment will be described. End effector assembly 40 is disposed at the distal end of catheter 30. End effector assembly 40 includes a first end effector 42 (e.g., first cutter or jaw) and a second end effector 44 (e.g., second cutter or jaw) provided at a distalmost end of end effector assembly 40. As shown in FIGS. 2, 3A, and 3B, first cutter 42 and second cutter 44 each include teeth 46, 48, respectively, opposing each other. Teeth 46 and 48 may have the same or different shapes, and may be spaced in any manner around the respective end effector 42, 44 for biopsy. Further, each set of teeth 46 and 48 may vary in number, size, and orientation on first cutter 42 and/or second cutter 44, respectively. As shown in FIG. 2, teeth 46 and 48 may overlap and/or fit together when in a closed position.

With continued reference to FIGS. 2 and 3A, cutter 42 further includes a first pin or protrusion 42a on a proximal tang 43 of cutter 42 at an end opposite teeth 46, first protrusion 42a being substantially perpendicular to axis A. Referring to FIGS. 2 and 3B, second cutter 44 includes a second pin or protrusion 44a, provided on a proximal tang 45 at an end opposite teeth 48 and substantially perpendicular to axis A. First cutter 42 includes a first hole 42b extending through tang 43 of first cutter 42 and substantially perpendicular to axis A. Second cutter 44 includes a second hole 44b extending through tang 45 of second cutter 44 and substantially perpendicular to axis A. As further shown in FIG. 3B, teeth 48 may surround a concave cup defining a hole 49. Hole 49 may allow fluid, debris, and other material to flow therethrough during grasping and cutting, as described herein, to, for example, allow for a greater volume of biopsy. First cutter 42 may include a similarly concave cup shaped and oriented hole as seen, for example, in FIGS. 8A and 8B. In some embodiments, first cutter 42 and second cutter 44 are identically configured, and assembled in end effector assembly 40 opposite of each other, such that teeth 46, 48 oppose each other and concave cup portions on each cutter define an area for receiving tissue. Identical components may reduce manufacturing costs and reduce or eliminate errors in assembly.

Figure 4:
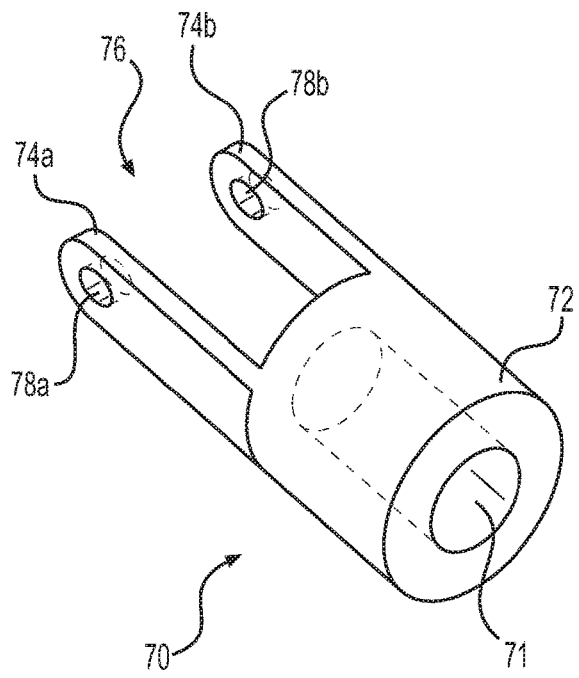
FIG. 4 is a perspective view of a clevis of the medical device of FIG. 2.

As shown in FIGS. 2 and 4, end effector assembly 40 further includes a clevis 70. Clevis 70 has a U-shape or a forked shape, with a proximal end 72 and two distally extending arms 74a, 74b. As shown in FIG. 4, a slot or notch 76 is provided between arms 74a, 74b, and is sized and positioned to receive various elements of end effector assembly 40, as will be described herein.

As further shown in FIG. 4, distal ends 74a, 74b each includes a through hole 78a, 78b, respectively, which are perpendicular to longitudinal axis A. Through holes 78a, 78b are sized and shaped to receive an axle pin 80. As shown in FIG. 2, axle pin 80 secures first cutter 42 and second cutter 44 to clevis 70. For example, first cutter 42 and second cutter 44 are inserted into notch 76 such that first hole 42b and second hole 44b line up with first hole 78a and second hole 78b. Axle pin 80 is then inserted through first hole 78a, first hole 42b, second hole 44b, and second hole 78b, and axle pin 80 is secured at each of first hole 78a and second hole 78b. For example, axle pin 80 can be fixed using an adhesive, sonic welding, laser welding, or any other attachment method known in the art. Further, since first hole 42b and second hole 44b are not fixed on axle pin 80, first cutter 42 and second cutter 44 are pivotally attached about axle pin 80, such that first cutter 42 and second cutter 44 may pivot about axle pin 80 and grasp and/or cut tissue, as will be described herein. A lumen 71 extends through proximal end 72 along longitudinal axis A from a proximalmost end to notch 76.

Figure 5A:
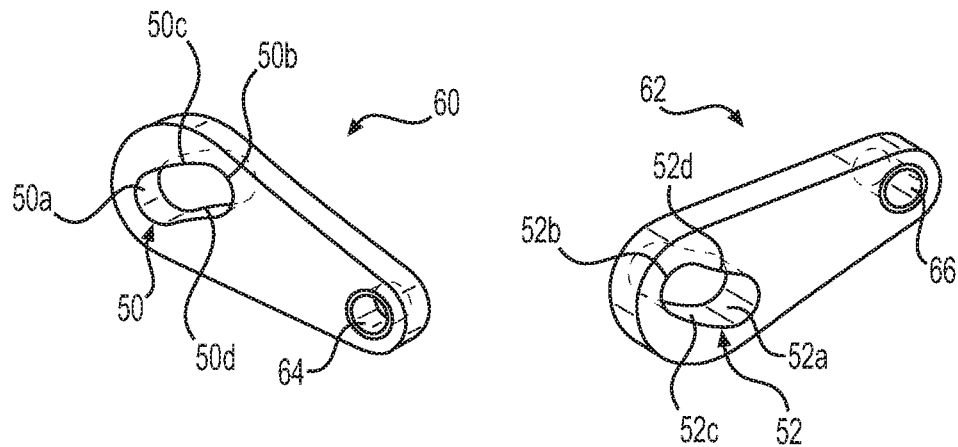
FIG. 5A is a perspective view of links of the medical device of FIG. 2.

End effector assembly 40 further includes a first link 60 and a second link 62. First link 60 and second link 62 will be described with reference to FIG. 5A. First link 60 and second link 62 each have curved proximal and distal ends, a radius of curvature of the curve of the proximal ends being greater than a radius of curvature of the curve at the distal ends. It will be understood, however, that the radii of curvatures are not limited hereto. For example, the radius of curvature of the curve of the proximal ends may be less than a radius of curvature of the curve at the distal ends, or the radii of curvatures may be equal. The curved proximal and distal ends are connected by substantially straight sidewalls, which taper from the proximal end to the distal end. First link 60 includes a first throughhole 64 at the distal end and a first slot 50 at the proximal end. Second link 62 also includes a second throughhole 66 at a first end thereof and a second slot 52 at an opposite end. As shown in FIG. 5A, first throughhole 64 extends through first link 60, but the configuration is not limited thereto. For example, first throughhole 64 may extend only partially into first link 60 (and second throughhole 66 may extend only partially into second link 62). As will be described in greater detail herein, first throughhole 64 and second throughhole 66 receive first protrusion 42a and second protrusion 44a, respectively. In some embodiments, first link 60 and second link 62 are identically configured, and assembled in end effector assembly 40 opposite of each other, such that slot sidewalls 50d, 52d are angled in opposite directions. Identical components may reduce manufacturing costs and reduce or eliminate errors in assembly.

With continued reference to FIG. 5A, a first slot 50 on first link 60 includes a curved surface, the curved surface facing first throughhole 64. For example, first slot 50 has a generally kidney-bean shape and includes sidewalls 50a-50d. Sidewalls 50a and 50b are concave in shape, the concave portions of sidewalls 50a and 50b generally facing each other. Generally, sidewall 50a is positioned further from throughhole 64 than sidewall 50b, but the arrangement is not limited thereto. As further shown in FIG. 5A, sidewalls 50c and 50d are similarly curved, with a convex surface of sidewall 50d facing slot 50 and toward a concave surface of sidewall 50c. Generally, sidewall 50d is positioned closer to throughhole 64 than sidewall 50c. A longitudinal axis of slot 50 extends through a center of walls 50a and 50b, and is transverse to an axis extending between centers of slot 50 and throughhole 64.

Second slot 52 on second link 62 includes a similar curved surface as slot 50. For example, sidewalls 52a-52d have a same orientation with respect to throughhole 66 as sidewalls 50a-50d have to throughhole 64. As will be described herein, first slot 50 and second slot 52 provide greater degrees of freedom to end effector assembly 40 to improve tissue grasping and/or cutting, and to allow for greater passability through tortuous passages.

Figure 5B:
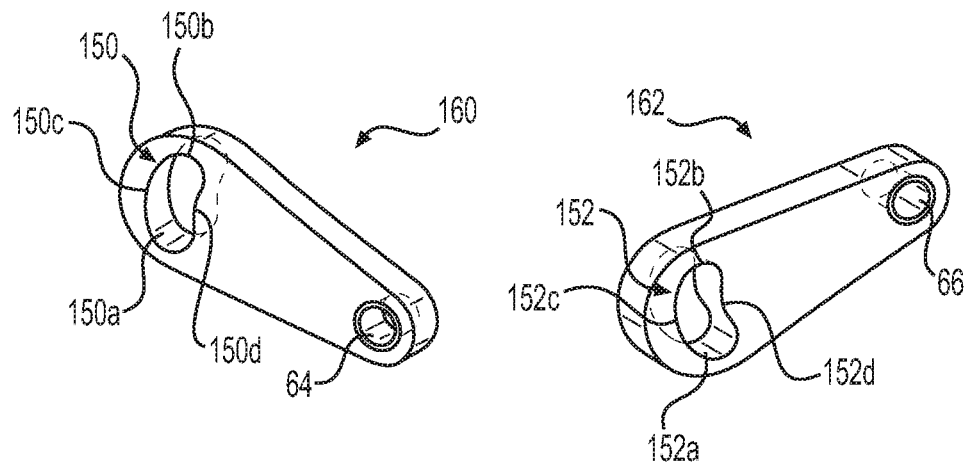
FIG. 5B is a perspective view of another embodiment of links to be used with the medical device of FIG. 2.

In another embodiment, a second set of links 160, 162 will be described with reference to FIG. 5B. Links 160, 162 have a similar size and shape as first link 60 and second link 62, respectively. Further, throughholes 64 and 66 are similarly provided in links 160 and 162, respectively. As shown in FIG. 5B, a slot 150 is provided in a link 160 and a slot 152 is provided in a link 162. For example, slot 150 includes sidewalls 150a-d. Similar to slot 50, slot 150 is generally kidney-bean shaped, with sidewalls 150a and 150b having concave surfaces generally facing each other, and a convex surface of sidewall 150d faces a concave surface of sidewall 150c. As further shown in FIG. 5B, slot 150 is generally oriented such that a concave surface of sidewall 150d generally faces throughhole 64. Slot 152 of link 162 has sidewalls 152a-d which are similarly arranged as sidewalls 150a-d. Further, slot 152 is oriented such that a concave surface of sidewall 152d generally faces throughhole 66. A longitudinal axis of slot 150, 152 extends through a center of walls 150a, 150b and 152a, 152b, respectively, and is substantially perpendicular to an axis extending between centers of slots 150, 152 and throughholes 64, 66, respectively. As described above, slot 150 and slot 152 provide greater degrees of freedom to end effector assembly 40 to improve tissue grasping and/or cutting, and to allow for greater passability through tortuous passages during insertion and/or removal from a body. Link 160 and link 162 may be substituted for first link 60 and second link 62, respectively.

Figure 6:
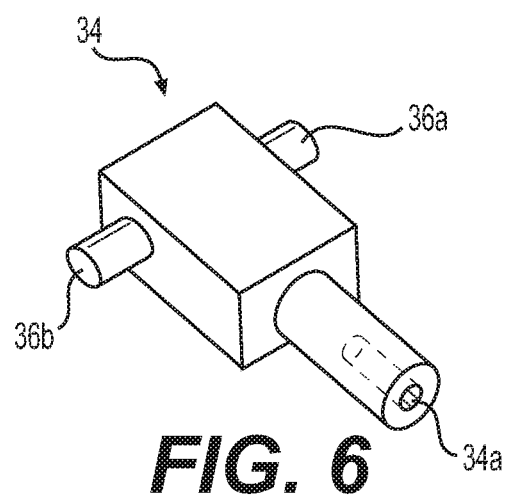
FIG. 6 is a perspective view of an actuator of the medical device of FIG. 2.

With reference to FIG. 6, an actuator 34 (e.g., a wire attachment) will be described. Actuator 34 includes a lumen 34a extending along longitudinal axis A, and which extends from a proximal end of actuator 34 at least partially into actuator 34. A distal end of actuator 34 includes a first protrusion or pin 36a and a second protrusion or pin 36b extending transverse to longitudinal axis A and in opposite directions from each other. A proximal end of actuator 34 is cylindrical in shape to slide within lumen 71, as will be described in greater detail. It will be understood that the shape is not limited thereto, however.

FIG. 2 illustrates a connection between actuator 34, first and second links 60, 62, and first and second cutters 42, 44. As described above, axle pin 80 is inserted through first hole 78a, first hole 42b, second hole 44b, and second hole 78b, and axle pin 80 is secured at each of first hole 78a and second hole 78b. The proximal end of first cutter 42 connects to the distal end of first link 60 via first protrusion 42a and first throughhole 64. For example, first protrusion 42a extends into first throughhole 64, such that first cutter 42 and first link 60 are pivotally connected to each other. Second link 62 and second cutter 44 are similarly pivotally attached via second protrusion 44a and second throughhole 66. First protrusion 42a and second protrusion 44a have an outer diameter equal to or less than an inner diameter of first throughhole 64 and second throughhole 66. It will be understood that the outer diameters of first protrusion 42a and second protrusion 44a and the inner diameters of first throughhole 64 and second throughhole 66 are not required to be the same size.

With continued reference to FIG. 2, a distalmost end of wire 32 is disposed at least partly within lumen 34a, and actuator 34 is fixed to wire 32 by, e.g., crimping, welding, adhesive, or any other manner known in the art. As further shown in FIG. 2, first protrusion 36a extends at least partly into first slot 50, thereby allowing first protrusion 36a to slide within first slot 50, as will be described in greater detail herein. According to an embodiment, an outer diameter of first protrusion 36a is equal to, or slightly less than, a distance between sidewalls of first slot 50, such that first protrusion 36a is guided along first slot 50 from a first end to a second end. While not shown, second protrusion 36b similarly extends at least partly into second slot 52, and second protrusion 36b slides within second slot 52 in a similar manner. A diameter of second protrusion 36b may be sized in a similar manner as first protrusion 36a, with respect to a distance between sidewalls of second slot 52.

An operation of end effector assembly 40 will now be described with reference to FIGS. 2 and 7A-8B.

Figure 7A:
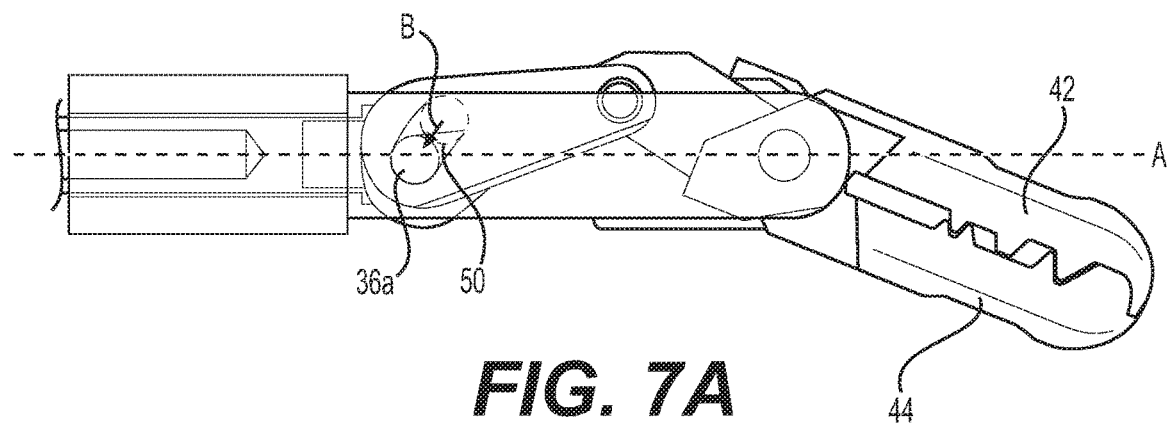
FIGS. 7A and 7B are views of the end effector assembly of the medical device of FIG. 2.
Figure 7B:
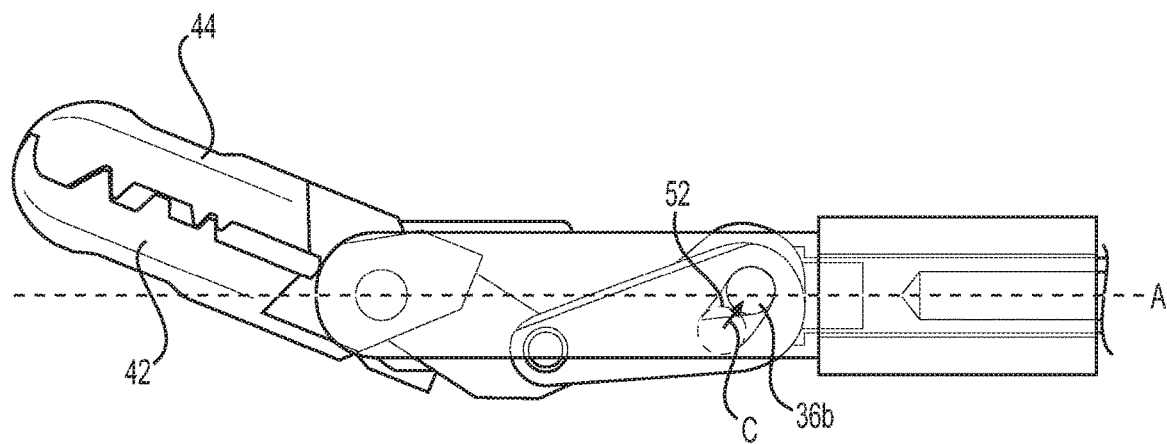

Referring first to FIG. 2, an embodiment of end effector assembly 40 with actuator 32 provided at a proximalmost location is shown. In this configuration, first cutter 42 and second cutter 44 are in a closed position. This configuration is generally used during an insertion or removal of end effector assembly 40 through a lumen of a body/patient, including passing end effector assembly 40 through a lumen of a catheter or scope. As shown in FIGS. 7A and 7B, end effector assembly 40, and specifically end effectors 42, 44 in a closed configuration, can pivot with respect to longitudinal axis A about axle pin 80 to navigate tortuous paths, with or without movement of wire 32 and/or an actuator. For example, as shown in FIG. 7A, first protrusion 36a slides from a first location (shown by the dotted lines) in slot 50 to a second location, as shown by arrow B. As first protrusion 36a slides within slot 50, second protrusion 36b slides from a first location (shown by dotted lines) in slot 52 to a second location, as shown by arrow C in FIG. 7B. This range of movement allows first cutter 42 and second cutter 44 to angle downward with respect to longitudinal axis A, as shown in FIGS. 7A and 7B. First protrusion 36a can slide back to the first position in slot 50 and second protrusion 36b can slide back to the first position in slot 52, thereby causing first cutter 42 and second cutter 44 to angle upward with respect to longitudinal axis A (not shown). This range of movement allows end effector assembly 40, and specifically end effectors 42, 44 in a closed configuration, to turn or rotate when navigating tortuous paths, which increases the target locations end effector assembly 40 is able to reach.

Figure 8A:
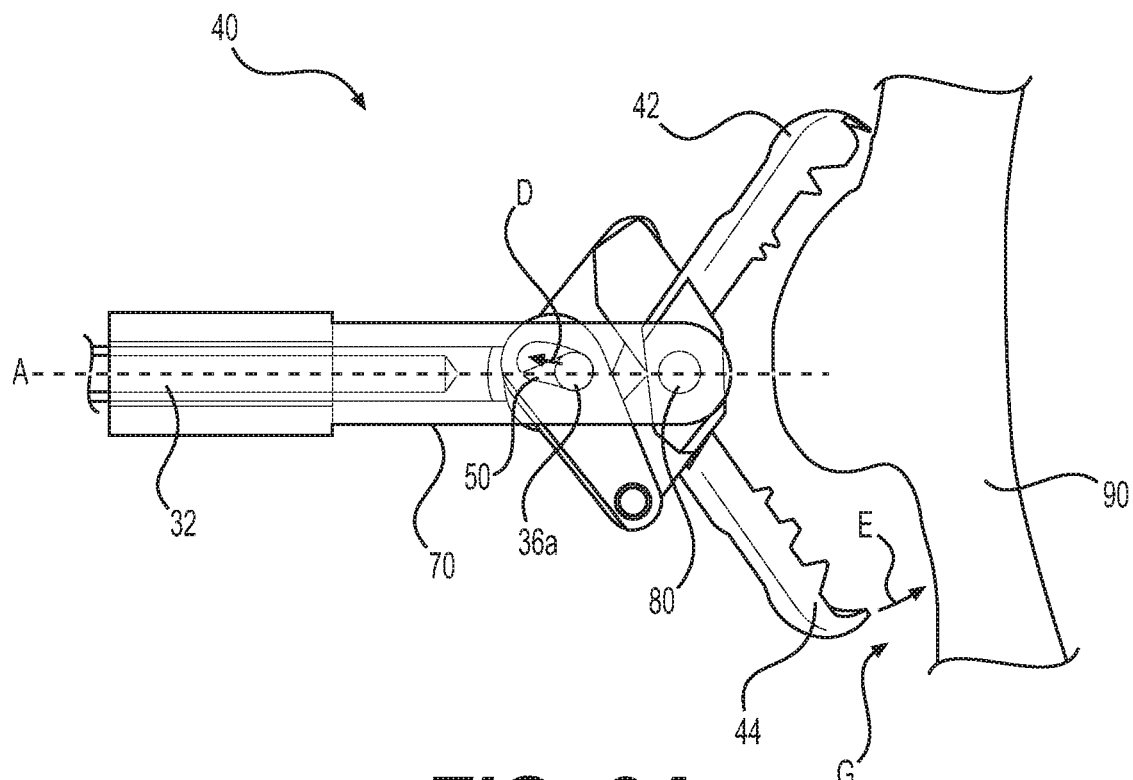
FIGS. 8A and 8B are views of an operation of the medical device of FIG. 2.
Figure 8B:
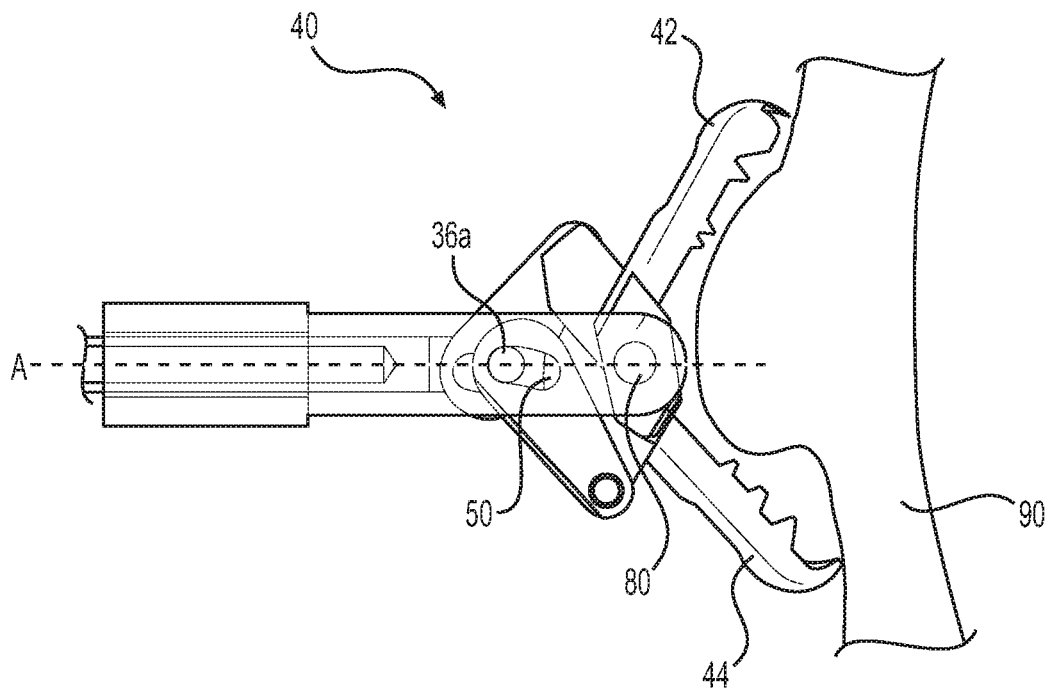

Once end effector assembly 40 reaches the target location, e.g., target 90 shown in FIGS. 8A and 8B, end effector assembly 40 is manipulated to grasp target 90. As shown in FIG. 8A, clevis 70 may be maintained in a stationary position while wire 32 is advanced distally. Alternatively, or additionally, clevis 70 may be advanced distally at a speed less than an advance speed of wire 32. Advancing wire 32 distally along longitudinal axis A causes first cutter 42 and second cutter 44 to move to an open position, where teeth 46, 48 of first cutter 42 and second cutter 44 do not contact one another. For example, moving wire 32 in the distal direction causes actuator 34 to push against first link 60 and push down on pin 42a, thereby forcing first cutter 42 up and open. At a same time, actuator 34 pushes against second link 62, thereby pushing up on pin 44a and forcing second cutter 44 down and open. After first cutter 42 and second cutter 44 are opened, end effector assembly is advance toward target 90.

As shown in FIG. 8A, target 90 may be an abnormal shape such both cutters 42, 44 do not simultaneously contact target 90 when end effector assembly 40 is originally advanced. For example, first cutter 42 contacts target 90, but a gap G is between second cutter 44 and target 90. To create a desired contact between both cutters 42, 44 of end effector assembly 40 and target 90, catheter 30 is advanced distally toward target 90. This additional movement causes first protrusion 36a to slide within slot 50, as shown by arrow D, and second protrusion 36b to slide within second slot 52, thereby rotating first cutter 42 and second cutter 44 about axle pin 80, which is perpendicular to longitudinal axis A, and eliminating gap G between second cutter 44 and target 90 (shown by arrow E), as shown in FIG. 7B. Once both first cutter 42 and second cutter 44 contact target 90, wire 32 is pulled proximally while a position of catheter 30 is maintained, to grasp and cut a portion of target 90 to be removed from the body. It will be understood that the portion of target 90 may be cut, resected, or otherwise removed from target 90. It will also be understood that target 90 may merely be manipulated, and no tissue may be removed from the body. End effector assembly 40 is subsequently removed from the patient's body.

First and second slots 50 and 52 further allow cutters 42, 44 to pivot about axle pin 80 independent of one another. When cutters 42, 44 are in an open configuration as shown in FIG. 8A, first cutter 42 and/or second cutter 44 may pivot about axle pin 80 independent of each other. For example, actuator 34, and consequently first protrusion 36*a* and second protrusion 36*b*, are maintained in a stationary position. Further, with reference to FIG. 8A, first cutter 42 contacts target 90 and maintains a stationary position. Second slot 52 of second link 62 can slide along second protrusion 36*b*, thereby pivoting second cutter 44 about axle pin 80. Alternatively, or additionally, second cutter 44 may maintain a stationary position and first cutter 42 can pivot about axle pin 80, by sliding first slot 50 along first protrusion 36*a*. In addition to the independent cutter movement in the open position, the structure of end effector assembly 40 also allows end effector assembly 40 to navigate a tortuous path encountered during removal, as set forth above.

Figure 9:
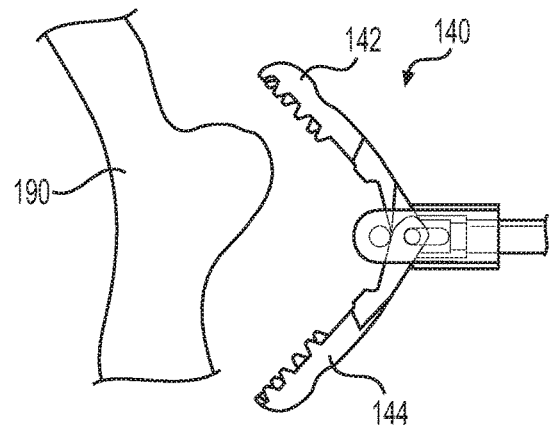
FIG. 9 is a view of an end effector assembly of a medical device according to another embodiment.

An embodiment according to another example is illustrated in FIG. 9. Like reference numerals will be used to denote like elements.

Figure 10:
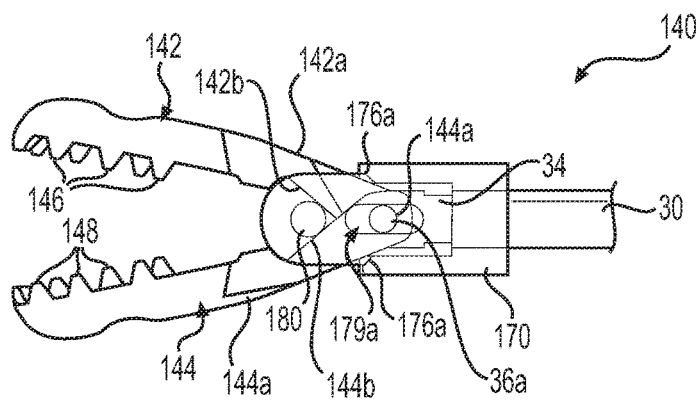
FIG. 10 is a plain view of the end effector assembly of the medical device of FIG. 9.

An end effector assembly 140 (e.g., biopsy assembly) is illustrated in FIG. 9. End effector assembly 140 may be used with a proximal manipulating device and a catheter, such as handle 20 and catheter 30 shown in FIG. 1. Referring to FIG. 10, end effector assembly 140 includes a first end effector 142 (e.g., first cutter), a second end effector 144 (e.g., second cutter), an actuator (e.g., actuator 34), and a clevis 170. First cutter 142 and second cutter 144 have teeth 146 and 148, respectively, similar to teeth 46, 48 described above. As with first cutter 42 and second cutter 44, first cutter 142 includes a first throughhole (not shown) in a proximal tang thereof, opposite teeth 146, and second cutter 144 includes a second throughhole 144*a* in a proximal tang thereof, opposite teeth 148.

Figure 11A:
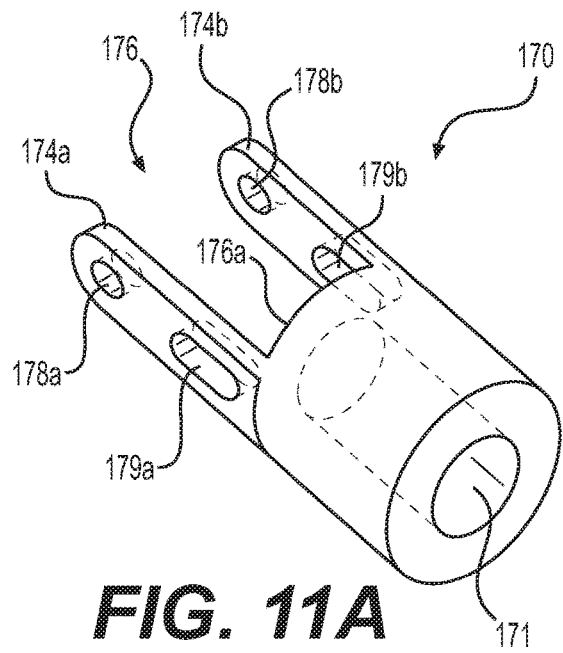
FIGS. 11A and 11B are views of a clevis of the medical device of FIG. 9.
Figure 11B:
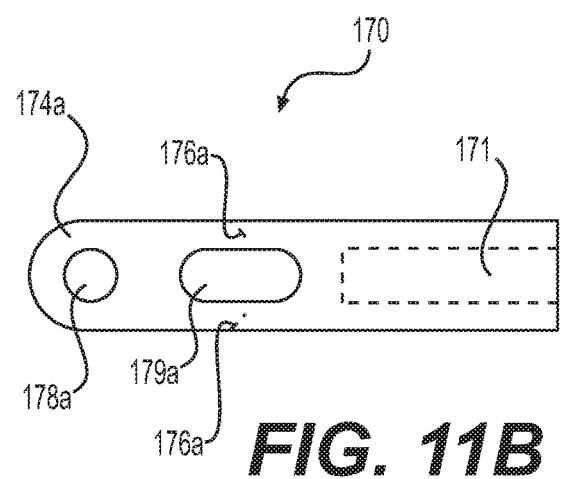

Clevis 170 has a similar design as clevis 70 of FIG. 1. For example, as shown in FIGS. 11A and 11B, clevis 170 includes distal arms 174*a*, 174*b* with a notch 176 formed therebetween and extending along longitudinal axis A. First hole 178*a* and second hole 178*b* are formed in respective distal arms 174*a*, 174*b* at a distal end of clevis 170. As shown in FIG. 10, an axle pin 180 is secured in first hole 178*a* and second hole 178*b*. Clevis 170 further includes a first longitudinal slot 179*a* and a second longitudinal slot 179*b*, each having a racetrack shape and extending along the longitudinal axis A of respective distal arms 174*a*, 174*b*, and exposed to notch 176. Slots 179*a*, 179*b* are proximal to slots 178*a*, 178*b*, respectively. As further shown in FIG. 10, clevis 170 includes tapered edges 176*a* at a proximal end of notch 176. As shown in FIG. 11B, tapered edges 176*a* limit a largest opening angle of first cutter 142 and second cutter 144. For example, when cutters 142, 144 are in an open configuration, a first surface 142*a* and a second surface 144*a* contact tapered edges 176*a* and prevent any further opening of cutters 142, 144. Further, tapered edges 176*a* allow first surface 142*a* and second surface 144*a* of first cutter 142 and second cutter 144, respectively, to slide along tapered edges 176 in a camming action, thereby assisting the closing of first cutter 142 and second cutter 144. A lumen 171 is positioned in clevis 170 in a similar manner to lumen 71 of clevis 70.

Actuator 34 as described above is also shown in FIG. 10, and is fixed to a distalmost portion of a wire or a cable passing through catheter 30, e.g., wire 32 shown in FIG. 1, as set forth herein. First protrusion 36*a* of actuator 34 passes through a first throughhole 144*a* of first cutter 144 and slides within first slot 179*a*, and second protrusion 36*b* of actuator 34 passes through a second throughhole (not shown) of second cutter 142 and slides within a second slot 179*b*. First protrusion 36*a* and second protrusion 36*b* have a diameter equal to or less than a distance between sidewalls of first slot 179*a* and second slot 179*b*, respectively. As will be described herein, this configuration allows first cutter 142 and second cutter 144 to pivot about actuator 34 (and specifically protrusions 36*a*, 36*b*) from a closed position to an open position, and allows first cutter 142 and second cutter 144 to be withdrawn at least partially into clevis 170 when first cutter 142 and second cutter 144 are in the closed position. A third surface 142*b* and a fourth surface 144*b* of first cutter 142 and second cutter 144, respectively, can each ride along pin 180, thereby opening first cutter 142 and second cutter 144. For example, the movements of third surface 142*b* and fourth surface 144*b* along pin 180 creates a camming operation that aids in opening and closing first and second cutters 142, 144. Moreover, in a closed configuration, third surface 142*b* and fourth surface 144*b* surround pin 180 to create a smaller profile of end effector assembly 140.

An operation of end effector assembly 140 will now be described with reference to FIG. 9. Similar to end effector assembly 40 described above, a catheter, e.g., catheter 30, including end effector assembly 140 at its distal end is advanced to a target 190. While catheter 30 remains stationary, distal actuation of wire 32 causes actuator 34 to move distally along longitudinal axis A. First protrusion 36*a* slides distally within first slot 179*a* and second protrusion 36*b* slides distally within second slot 179*b*, causing third surface 142*b* and fourth surface 144*b* of first cutter 142 and second cutter 144, respectively, to each ride along pin 180 in a camming motion, thereby opening first cutter 142 and second cutter 144. When end effector assembly 140 achieves a completely open configuration, first protrusion 36*a* and second protrusion 36*b* are disposed in their respective slots 179*a*, 179*b*, adjacent pin 180, and protrusions 36*a*, 36*b* and pin 180 are separated only by a portion of first cutter 142 and second cutter 144, respectively as shown in FIG. 9. The proximity of first protrusion 36*a* and second protrusion 36*b* to pin 180, as well as the angle of tapered edges 176*a*, achieve a large opening configuration which is more suitable for grasping and/or cutting target 190, which has an abnormal shape. As discussed above, once first and second cutters 142, 144 contact target 190, wire 32 is pulled proximally while maintaining a position of catheter 30, to grasp and cut a portion of target 190 to be removed from the patient. As first and second cutters 142, 144 are closed, third surface 142*a* and fourth surface 144*a* contact tapered edges 176*a* in the camming action, which assists the closing of first and second cutters 142, 144. It will be understood that the portion of target 190 may be cut, torn, or otherwise removed from target 190. It will also be understood that target 190 may merely be manipulated, and no tissue may be removed from the body. End effector assembly 140 is subsequently removed from the patient's body.

It will be understood that, unless specifically set forth herein, any material known in the art may be used for the various elements. For example, features may include a medical grade plastic or rubber, a ceramic, a metal, or a combination thereof.

It will be apparent to those skilled in the art that various modifications and variations can be made to the disclosed device without departing from the scope of the disclosure. For example, the configuration of pins and slots and the movements associated with end effector assemblies including these configurations may be used with any end effectors, including scissors, graspers, forceps, or the like. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
    opposing first and second end effectors coupled together and configured to move from an open configuration to a closed configuration;
    a first link having a distal end pivotally connected at a first position on the first end effector at a proximal end of the first end effector via a throughhole extending at least partially through the first link at the distal end and receiving a protrusion of the first end effector located at the proximal end of the first end effector, the first link including a first slot at a proximal end of the first link;
    a second link having a distal end pivotally connected at a first position on the second end effector at a proximal end of the second end effector via a throughhole extending at least partially through the second link at the distal end and receiving a protrusion of the second end effector located at the proximal end of the second end effector;
    a first actuator pin slidable within the first slot; and
    a clevis including a central longitudinal axis and a pair of distally extending and spaced apart arms, wherein a pivot pin is attached to each of the pair of arms, wherein each of the first and second end effectors is pivotally connected to the pivot pin at a second position of each of the first and second end effectors that is different than each of the first positions on the respective first and second end effectors;
    wherein, when the first actuator pin is stationary and the first and the second end effectors remain in the closed configuration, the first slot is movable over the first actuator pin and the first and second end effectors are configured to pivot about an axis of the pivot pin, causing a distal tip of one of the first and second end effectors to cross the central longitudinal axis of the clevis.

2. The medical device according to claim 1, wherein the second link includes a second slot at a proximal end thereof, and further comprising a second actuator pin, connected to the first actuator pin, and slidable within the second slot.

3. The medical device according to claim 2, wherein the first slot moves over the first actuator pin when the first actuator pin is stationary and when the first and the second end effectors are in the open configuration, and the first end effector pivots about the axis of the pivot pin while the second end effector remains stationary, and
    wherein the second slot moves over the second actuator pin when the second actuator pin is stationary and when the first and the second end effectors are in the open configuration, and the second end effector pivots about the axis of the pivot pin while the first end effector remains stationary.

4. The medical device according to claim 2, wherein the second slot moves over the second actuator pin when the second actuator pin is stationary, and the first and the second end effectors pivot about the axis of the pivot pin when in the closed configuration.

5. The medical device according to claim 2, wherein each of the first slot and the second slot is curved.

6. The medical device according to claim 1, wherein the first slot includes two concave ends, the concave ends facing each other and connected by a first concave sidewall and a second convex sidewall opposite the first concave sidewall, a longitudinal axis of the first slot extends through a center of the concave ends, and the first slot is angled with respect to the distal end of the first link such that the longitudinal axis of the first slot is traverse to a central axis of the first link extending thorough a center of the throughhole at the distal end of the first link and a center of the first slot.

7. The medical device according to claim 1, further comprising:
    a catheter including a lumen extending along a longitudinal axis of the catheter, the catheter being connected to the first and second end effectors at a distal end of the catheter; and
    a wire extending through the lumen and coupled to the first actuator pin, wherein movement of the wire along the longitudinal axis causes the first and the second end effectors to move between the open configuration and the closed configuration.

8. The medical device according to claim 7, wherein distal ends of the first and second end effectors are configured to rotate to a first position above the longitudinal axis of the catheter and to a second position below the longitudinal axis of the catheter, when the first and second end effectors are in the closed configuration.

9. The medical device according to claim 1, wherein the first slot includes two concave ends, the concave ends facing each other and connected by a first concave sidewall and a second convex sidewall opposite the first concave sidewall, a longitudinal axis of the first slot extends through a center of the concave ends, and the first slot is substantially parallel to the throughhole extending at least partially through the first link at the distal end of the first link such that the longitudinal axis of the first slot is perpendicular to a central axis of the first link extending through a center of the throughhole and a center of the first slot.

10. The medical device of claim 1, wherein, when the first and second end effectors are in the closed configuration and the first actuator pin is in a middle of the first slot, the first and second end effectors are approximately parallel with the central longitudinal axis of the clevis.

11. The medical device of claim 1, wherein the second link includes a second slot at a proximal end of the second link; wherein the medical device includes a second actuator pin slidable within the second slot; wherein, when the first actuator pin and second actuator pin are both stationary and the first and the second end effectors are in the closed configuration, the first slot is movable over the first actuator pin and the second slot is movable over the second actuator pin causing the first and second end effectors to transition from the closed configuration to the open configuration.

12. The medical device of claim 11, wherein the first position on the first end effector includes the protrusion of the first end effector located at a proximal end of the first end effector, and a distal end of the first link is pivotally connected to the first end effector via a throughhole extending at least partially through the first link at the distal end and receiving the protrusion of the first end effector at the first position; and wherein the first position on the second end effector includes the protrusion of the second end effector located at a proximal end of the second end effector, and a distal end of the second link is pivotally connected to the second end effector via a throughhole extending at least partially through the second link at the distal end and receiving the protrusion of the second end effector at the first position.

13. A medical device, comprising:
opposing first and second end effectors coupled together and configured to move from a fully open configuration to a closed configuration, wherein the first end effector includes a first plurality of teeth, the second end effector includes a second plurality of teeth opposing the first plurality of teeth, and the first plurality of teeth contact the second plurality of teeth when the first and second effectors are in the closed configuration;
a first link pivotally connected to the first end effector at a first position on the first end effector and having a tapered width along a length of the first link, the first link including a first slot at a proximal end of the first link;
a first actuator pin slidable within the first slot;
a second link pivotally connected to the second end effector at a first position on the second end effector and having a tapered width along a length of the second link the second link including a second slot at a proximal end of the second link;
a second actuator pin slidable within the second slot; and
a clevis including a central longitudinal axis, the clevis including a body and a pair of arms extending distally from the body and defining a slot between the pair of arms, each of the pair of arms including a hole, wherein a pivot pin is fixedly attached to the hole at a second position in each of the pair of arms that is different from the first position, the clevis further including a pair of sidewalls at a proximal end of the slot where the slot meets the body, wherein the sidewalls are transverse to the central longitudinal axis of the clevis and restrict the first and the second end effectors from opening past the fully open configuration;
wherein, when the first actuator pin is stationary and the first and the second end effectors remain in the closed configuration, the first slot is movable over the first actuator pin and the first and second end effectors are configured to pivot about an axis of the pivot pin, causing a distal tip of one of the first and second end effectors to cross the central longitudinal axis of the clevis.

14. The medical device of claim 13, wherein the second position is distal to the first position on each of the first and the second end effectors,
wherein when both the first slot moves over the first actuator pin when the actuator pin is stationary and the second slot moves over the second actuator pin when the second actuator pin is stationary, the first and second end effectors transition from the closed configuration to an open configuration.

15. The medical device of claim 13, wherein the first position on the first end effector includes a protrusion of the first end effector located at a proximal end of the first end effector, and a distal end of the first link is pivotally connected to the first end effector via a throughhole extending at least partially through the first link at the distal end and receiving the protrusion of the first end effector at the first position; and wherein the first position on the second end effector includes a protrusion of the second end effector located at a proximal end of the second end effector, and a distal end of the second link is pivotally connected to the second end effector via a throughhole extending at least partially through the second link at the distal end and receiving the protrusion of the second end effector at the first position.

16. The medical device of claim 13, wherein:
a first width of the first link at a proximal end of the first link is greater than a second width of the first link at a distal end of the first link, the distal end of the first link being pivotally connected to the first end effector; and
a first width of the second link at a proximal end of the second link is greater than a second width of the second link at a distal end of the second link, the distal end of the second link being pivotally connected to the second end effector.

17. A medical device, comprising:
opposing first and second end effectors coupled together and configured to move from an open configuration to a closed configuration;
a first link, wherein the first end effector is pivotally connected to a distal end of the first link at a first position on a proximal end of the first end effector, the first link including a first slot at a proximal end of the first link configured to receive a first actuator pin slidable within the first slot between a first end and a second end of the first slot;
a second link, wherein the second end effector is pivotally connected to a distal end of the second link at a first position on a proximal end of the second end effector, the second link including a second slot at a proximal end of the second link configured to receive a second actuator pin slidable within the second slot between a first end and a second end of the second slot, and wherein each of the first slot of the first link and the second slot of the second link is a curved slot including two concave ends facing each other that are connected by a first concave sidewall and a second convex sidewall opposite the first concave sidewall; and
a clevis including a central longitudinal axis and a pair of distally extending and spaced apart arms, wherein a pivot pin is attached to each of the pair of arms, wherein each of the first and second end effectors is pivotally connected to the pivot pin at a second position of each of the first and second end effectors that is different than each of the first positions on the respective first and second end effectors;
wherein, when the first actuator pin is stationary and the first and the second end effectors remain in the closed configuration, the first slot is movable over the first actuator pin and the first and second end effectors are configured to pivot about an axis of the pivot pin, causing a distal tip of one of the first and second end effectors to cross the central longitudinal axis of the clevis.

18. The medical device of claim 17, wherein each of the first and second end effectors includes a hole extending through the first and second end effectors at the second position, each of the pair of arms including a hole with which the hole of each the first and second end effectors is aligned to receive the pivot pin that is fixedly attached to the hole in each of the pair of arms such that the first and second end effectors are pivotally connected about an axis of the pin.

19. The medical device of claim 17, further comprising:
a catheter connected to the first end effector and the second end effector at a distal end of the catheter, wherein:
when the first end effector and the second end effector are in the open configuration and surrounding a target, the first actuator pin is positioned at the second end of the first slot and the second actuator pin is positioned at the second end of the second slot, and
when a gap remains between at least one of the first end effector and the second end effector in the open configuration and the target, a distal advancement of the catheter causes the first actuator pin to slide from the second end to the first end of the first slot and the second actuator pin to slide from the second end to the first end of the second slot, which rotates the first end effector and the second end effector about an axle pin pivotally connecting the first end effector and the second end effector to the distal end of the clevis to remove the gap.

* * * * *